(12) United States Patent
Zhang et al.

(10) Patent No.: US 8,133,873 B2
(45) Date of Patent: Mar. 13, 2012

(54) RECOMBINANT CHEMOKINE-ANTIGEN VACCINE

(75) Inventors: Shuren Zhang, Beijing (CN); Chen Lin, Beijing (CN); Wenxin Sun, Beijing (CN); Hanjun Qin, Beijing (CN); Chunxia Zhou, Beijing (CN); Xiao Liang, Beijing (CN); Dongmei Wang, Beijing (CN); Wenbo Ma, Beijing (CN); Xueyan Zhang, Beijing (CN); Ming Fu, Beijing (CN)

(73) Assignee: Cancer Institute, Chinese Academy of Medical Sciences, Beijing (CN)

( * ) Notice: Subject to any disclaimer, the term of this patent is extended or adjusted under 35 U.S.C. 154(b) by 821 days.

(21) Appl. No.: 11/596,100

(22) PCT Filed: May 9, 2005

(86) PCT No.: PCT/CN2005/000639
§ 371 (c)(1),
(2), (4) Date: Feb. 14, 2007

(87) PCT Pub. No.: WO2005/108584
PCT Pub. Date: Nov. 17, 2005

(65) Prior Publication Data
US 2009/0209729 A1    Aug. 20, 2009

(30) Foreign Application Priority Data
May 10, 2004   (CN) .......................... 2004 1 0037910

(51) Int. Cl.
*C07H 21/04* (2006.01)
*C07K 14/00* (2006.01)
*C07K 14/435* (2006.01)
*C07K 16/46* (2006.01)
*A61K 48/00* (2006.01)

(52) U.S. Cl. ................... 514/44 R; 530/350; 530/387.1; 530/806; 536/23.1; 536/23.4

(58) Field of Classification Search .................. None
See application file for complete search history.

(56) References Cited

U.S. PATENT DOCUMENTS
7,217,700 B2 * 5/2007 Vicari et al. ................ 514/44 R 2002/0034494 A1 * 3/2002 Vicari et al. ................ 424/85.1
2003/0008840 A1 * 1/2003 Vicari et al. .................... 514/44

FOREIGN PATENT DOCUMENTS
| WO | WO/0127146 A2 | 4/2001 |
| WO | WO/0152884 A1 | 7/2001 |
| WO | WO/02058723 A2 | 8/2002 |
| WO | WO-03/055439 A2 * | 7/2003 |

OTHER PUBLICATIONS

You et al. A retrogen strategy for presentation of an intracellular tumor antigen as an exogenous antigen by dendritic cells induces potent antitumor T helper and CTL responses. Cancer Res 61: 197-205, 2001.*
You et al. Induction of vigorous helper and cytotoxic T cell as well as B cell responses by dendritic cells expressing a modified antigen targeting receptor-mediated internalization pathway. J Immunol 165: 4581-4592, 2000.*
Rafiq et al. Immune complex-mediated antigen presentation induces tumor immunity. J Clin Invest 110:71-79, 2002.*
Yang et al. Intratumoral administration of dendritic cells overexpressing CCL21 generates systemic antitumor responses and confers tumor immunity. Clin Cancer Res 10: 2891-2901, 2004.*
Qin et al. Enhancement of antitumor immunity by a novel chemotactic antigen DNA vaccine encoding chemokines and multiepitopes of prostate-tumour-associated antigens. Immunology 117: 419-430, 2006.*
Terando et al. Chemokine gene vaccine modification of human dendritic cell-based tumor vaccines using a recombinant adenoviral vector. Cancer Gene Therapy 11: 165-173, 2004.*
Liu et al. Enhancement of DNA vaccine potency by sandwiching antigen-coding gene between secondary lymphoid tissue chemokine (SLC) and IgG Fc fragment genes. Cancer Biol & Therapy 5(4): 427-434, 2006.*
Dictionary definition for "glycin" from allwords.com.*
"Vaccine" definition entry; downloaded from Stedman's Medical Dictionary 28th Edition on Jun. 30, 2011; pp. 1-3.*
"Vaccine" definition entry; downloaded from Britannica Online Encyclopedia on Jun. 30, 2011; pp. 1-2.*

* cited by examiner

*Primary Examiner* — Bridget E Bunner
(74) *Attorney, Agent, or Firm* — Cozen O'Connor

(57) ABSTRACT

A recombinant gene sequence that comprises human SLC gene, antigen gene, and IgG1-Fc fragment gene, wherein the SLC gene is linked upstream to the antigen gene, and the IgG1-Fc fragment is linked downstream to the antigen gene. This invention also relates to the application of the recombinant gene sequence in the preparation of gene vaccine.

9 Claims, 8 Drawing Sheets

RECOMBINANT CHEMOKINE-ANTIGEN VACCINE

RELATED APPLICATIONS

This is a U.S. national stage of application No. PCT/CN2005/000639 filed May 9, 2005.

FIELD OF THE INVENTION

The invention relates to a new recombinant gene sequence, a fusion protein expressed from the gene, and vaccines produced with the gene, as well as to different gene vaccines produced by replacing the antigen gene in the recombinant sequence, or to use of the expression products as fusion peptide vaccines.

BACKGROUND OF THE INVENTION

Human secondary lymphoid tissue chemokine (SLC) has been paid much attention since its discovery. SLC regulates the secretion of cytokines, alters the immunosuppression states of the microenvironment of tumor, and promotes the development of Th1. Thus, SLC is useful in anti-tumor immunity. Further, SLC has effect in attracting the lymphocytes and dendritic cells (DC). The intratumor injection induces the local and systematic anti-tumor immune responses. SLC can also regulate the suppression of angiogenesis in the tumors. Thus, SLC is very useful in cancer immunotherapy. However, use of SLC protein alone or transgenic method did not show satisfactory results in anti-tumor immunity. Si-Yi Chen et al. have suggested that anti-tumor immunoreaction can be enhanced by immunizing mice with DCs that are transfected with recombinant retrovirus vector containing genes encoding IgG Fc fragment and tumor antigen. The mechanism is that the fusion protein secreted and expressed from DC is re-captured by DCs through the Fc receptor (FcR), and then the fusion protein epitope is presented to T helper cells (Th) through MHC class II molecules and cross presented to cytotoxic T lymphocytes (CTL) through MHC class I molecules, through which anti-tumor humoral-and-cellular immunity is induced systematically. Serre K et al. have reported that capacity of DC in capturing antigens through FcR-mediating endocytosis is 10,000 times higher than that through pinocytosis. However, the isolation, amplification and gene transfection of DC increase the complexity of the vaccine production. In this case, the DCs have to be prepared individually, which hampered the quality control and industrial production.

SUMMARY OF THE INVENTION

To overcome the disadvantage of the prior arts, one aim of the invention is to provide a new recombinant gene sequence.

Another aim of the invention is to provide a fusion protein expressed by the recombinant gene sequence.

Another aim of the invention is to provide a gene vaccine of the fusion protein encoded by the recombinant gene sequence according to the invention.

Furthermore, the aim of the invention is to provide a recombinant tumor chemotactic antigen gene vaccine.

To accomplish the aims of the invention, the following technique solutions are adopted:

The invention relates to a recombinant gene sequence, comprising human SLC gene, antigen gene, and IgG1-Fc fragment gene, wherein the SLC gene is linked upstream to the antigen gene, and the IgG1-Fc fragment gene is linked downstream to the antigen gene. The said antigen gene comprises Her2/neu, P53, PSA, PAP, PSM, MAGE1, MAGE2, MAGE3, BAGE, GAGE1, GAGE 2, CAG3, RAGE, NY-ESO-1, Tyrosinase, CEA, Ig idiotype, gp100, melan A, gp75, TRP-1, TRP-2, CDK4, CASP-8, ras, bcr/abl, MUC-1, and genes encoding the proteins related with the viruses of HCV, HIV and pathogenic microorganisms.

In the recombinant gene sequence according to the invention, EcoRI restrictive endonuclease sites and genes of three glycins are present between SLC gene and antigen gene, and EcoRV restrictive endonuclease sites and genes of five glycins are present between antigen gene and IgG1-Fc fragment gene.

The recombinant gene sequence of the invention comprises SEQ ID NO:1 and SEQ ID NO: 12.

The invention also relates to an amino acid sequence encoded by the recombinant gene sequence according to the invention. The said amino acid sequence comprises SEQ ID NO: 2.

The invention also relates to an amino acid sequence encoded by SEQ ID NO: 12. The said amino acid sequence is SEQ ID NO: 13.

The invention also relates to a gene vaccine, comprising the recombinant gene sequence of the invention.

In addition, the invention also relates to a gene vaccine. Preferably, the gene vaccine comprises SEQ ID NO: 1, SEQ ID NO: 12 and the corresponding amino acid sequences.

In other words, the invention relates to a recombinant gene sequence, comprising human SLC gene, antigen gene, and IgG1-Fc fragment gene, wherein the SLC gene is linked upstream to the antigen gene, and the IgG1-Fc fragment gene is linked downstream to the antigen gene. The said antigen gene comprises Her2/neu, P53, PSA, PAP, PSM, MAGE1, MAGE2, MAGE3, BAGE, GAGE1, GAGE 2, CAG3, RAGE, NY-ESO-1, Tyrosinase, CEA, Ig idiotype, gp100, melan A, gp75, TRP-1, TRP-2, CDK4, CASP-8, ras, bcr/abl, MUC-1, and other genes encoding the proteins related with the viruses of HCV, HIV and other pathogenic microorganisms. EcoRI restrictive endonuclease sites and genes of three glycins are present between SLC gene and antigen gene of the invention, and EcoRV restrictive endonuclease sites and genes of five glycins are present between antigen gene and IgG1-Fc fragment gene.

This invention also relates to the use of the recombinant gene sequence of the invention in preparing gene vaccines. Namely, a gene vaccine, comprising the gene sequence of the invention, in particular, SEQ ID NO: 1, SEQ ID NO: 12 and the corresponding amino acid sequences of SEQ ID NO: 2 and SEQ ID NO: 13.

In other words, this invention relates to a recombinant gene sequence, comprising human SLC gene, antigen gene and IgG1-Fc fragment gene (See FIG. 13). SLC gene is linked upstream to the antigen gene, and the EcoRI restrictive endonuclease sites and genes of three glycins are introduced. IgG1-Fc fragment gene is linked downstream to the antigen gene, and EcoRV restrictive endonuclease sites and genes of five glycins are introduced.

According to the invention, replacing the antigen gene in the said genes through the restrictive endonuclease sites can produce various chemotactic antigen fusion genes. In particular, this invention relates to a recombinant gene comprising the nucleic acid sequence of SEQ ID NO: 1. The nucleic acid sequence of SEQ ID NO: 1 is the artificially ligated sequence of SLC-Her2/P53-Fc, wherein the SLC gene locates from position 1 to position 402 of the nucleic acid; the Her2 ligating gene locates from position 418 to position 711 of the nucleic acid. The nucleic acids from position 418 to position 444 in the recombinant gene are corresponding to those from position 1105 to position 1131 in the open reading frame (ORF) of Her2/neu gene. The nucleic acids from position 445 to position 546 in the recombinant gene are corresponding to those from position 244 to position 345 in the open reading frame (ORF) of Her2/neu gene, wherein a mutation from G to C at position 250 is introduced. The nucleic acids from position 547 to position 711 in the recombinant gene are corresponding to those from position 1333 to position 1479 in the ORF of Her2/neu gene. In the recombinant gene, part of P53 gene locates from position 712 to position 1113, corresponding to the nucleic acids from position 475 to position 876 of p53 ORF. The IgG Fc gene (including introns) locates from position 1147 to position 2057 in the recombinant gene, wherein the two introns locates from position 1189 to position 1309, and from position 1640 to position 1739, respectively. The nucleic acid sequence from position 1147 to position 1189 is the C-region hinge sequence. The nucleic acid sequence from position 1310 to position 1369 is for CH2, and nucleic acid sequence from position 1740 to position 2057 is for CH3. Three genes of glycins and EcoRI restrictive endonuclease sites are introduced upstream to Her2/P53 fragment, and five genes of glycins and EcoRV restrictive endonuclease sites are introduced downstream to Her2/P53. According to this invention, to make the biology function of expressed factors normal, 3~5 genes of glycins are introduced upstream and downstream to the antigen gene. The effect of the glycin genes is to prevent the recombinant antigen from interfering the three-dimensional structure.

This invention also relates to an amino acid sequence (612aa, mat589aa) of SEQ ID NO: 2 encoded by nucleotide sequence of SEQ ID NO: 1, wherein SEQ ID NO: 1 is an artificially recombinant SLC-Her2/P53-Fc gene. In the said amino acid sequence, SLC fragment locates from position 1 to position 134, three glycins locate from position 135 to position 137, and part of Her2 peptide locates from position 140 to position 237. The amino acids from position 140 to position 148 in the fusion protein are corresponding to those from position 369 to position 377 in Her2/neu. The amino acids from position 149 to position 182 in the fusion protein are corresponding to those from position 82 to position 115 in Her2/neu, wherein a mutation from V to L is introduced at position 84. The amino acids from position 183 to position 238 in the fusion protein are corresponding to those from position 445 to position 499 in Her2/neu. Part of P53 peptide locates from position 238 to position 371 in the fusion protein (corresponding to the amino acids from position 159 to position 292 in P53 natural form). The five glycins locate from position 374 to position 378. The IgG Fc locates from position 383 to position 612, wherein the sequence from position 383 to position 396 is for C-region hinge, the sequence from position 397 to position 506 is for CH2, and the sequence from position 507 to position 612 is for CH3.

This invention also relates to another recombinant gene for prostate cancer vaccine, the sequence of which is shown by SEQ ID NO: 12. The nucleotide sequence of SEQ ID NO: 12 is a sequence of artificially ligated SLC-PSM-mPAP-PSA-Fc (SLC-3P-Fc) gene, wherein only partial sequences of PSM (human Prostate Specific Membrane Antigen), mPAP (mouse Prostatic Acid Phosphatase), and PSA (human Prostate Specific Antigen) are introduced. In the fusion gene, SLC gene locates from position 1 to position 402; Part of PSM gene locates from position 418 to position 603, corresponding to the sequence from position 1987 to position 2172 in the PSM open reading frame (ORF); The mPAP gene locates from position 604 to position 759, corresponding to the sequence from position 328 to position 484 in mPAP ORF; PSA gene locates from position 760 to position 981, corresponding to the sequence from position 151 to position 372 in PSA ORF; The IgG Fc gene (including introns) locates from position 1003 to position 1925, wherein the two introns locate from position 1057 to position 1177 and from position 1508 to position 1607, respectively. Genes for three glycins and EcoRI restrictive endonuclease sites are introduced upstream to 3P, and genes for five glycins and EcoRV restrictive endonuclease sites are introduced downstream to 3P.

This invention also relates to the amino acid sequence of SEQ ID NO: 13 encoded by nucleotide sequence of SEQ ID NO: 12. Namely, the invention relates to the amino acid sequence (568aa) corresponding to the artificially recombinant SLC-3P-Fc gene. In this fusion amino acid sequence, SLC locates from position 1 to position 134, three glycins locates from position 135 to position 137, PSM locates from position 140 to position 201, part of mPAP peptide locates from position 202 to position 253, part of PSA peptide locates from position 254 to position 327, five glycins locates from position 374 to position 378, and IgG1-Fc locates from position 335 to position 568.

This invention also relates to the use of the recombinant gene sequence of the invention, including SEQ ID NO: 1, in preparing vaccines.

As can be seen from above, the strategy for the chemotactic antigen of the invention is as follow: linking the chemokine of SLC upstream to the antigen and linking the Fc of IgG downstream to the antigen; introducing the three parts-fused gene directly into healthy or tumor tissues for expression and secretion; and forming a two-part conjoined body through Fc hinge region. The said recombinant protein actively attracts DC and T cells through the chemotactic activity of SLC in vivo. DC captures the fusion protein with high efficiency through pinocytosis, especially with the help of Fc receptor and SLC receptor CCR7. Meanwhile, DC carries the antigen into the cell. After being processed and treated, the antigen is presented to Th and CTL through MHC-II or MHC-I molecule. Finally, specific anti-tumor humoral and cellular immune response is induced completely. In addition, DC can be activated by the combination of Fc fragment with Fc receptor of DC. SLC can actively abstract DC and T lymphocytes, as well as promotes the secretion of cytokines such as IL-12, IFN-γ, and interferon-induced protein (IP-10), promotes the development of Th1, down-regulats the production of TGF-β and VEGF. Thus, SLC is very useful in anti-tumor immunity. For the reason mentioned above, such combination has synergistical effect and can induce stronger anti-tumor immune response (See FIG. 1).

In this invention, different recombinant genes are used, but not intending to restrict the invention. The study for control has revealed that either in the form of plasmid or in the form fusion protein, the recombinant chemokine antigen can be produced industrially. The step of preparation of DC has been omitted in the application. However, DC can be targeted with high efficiency in vivo. Moreover, introduction of restrictive endonuclease sites into the two ends of antigen gene makes it possible to replace the antigen to produce various chemokine antigen vaccines against tumorous or non-tumorous diseases. For example, a new chemokine antigen vaccine can be produced by replacing the HP antigen in SLC-HP-Fc with prostate cancer-relating antigen.

The recombinant gene can be constructed into the eukaryotic vectors by using direct injection of the plasmid into the body or tumor. Other techniques such as gene gun and electrical pulse can enhance the transfection rate and expression efficiency. Constructed recombinant virus, such as retrovirus, adenovirus, adeno-associated virus, vaccine virus, herpes simplex virus and so on, can also be used as vaccine for in vivo injection. The plasmid can be transfected into Eukaryotic cell (for example, CHO) and cultured in vitro for secretion and expression. Through the Fc fragment, the fusion protein can be easily and efficiently isolated and purified by Affinity Chromatography method, and can be used as protein vaccine.

BRIEF DESCRIPTION OF THE DRAWINGS

FIG. 15 discloses "3~5 Glycins" as SEQ ID NO: 41.

DETAILED DESCRIPTION OF THE INVENTION

Figure 1:
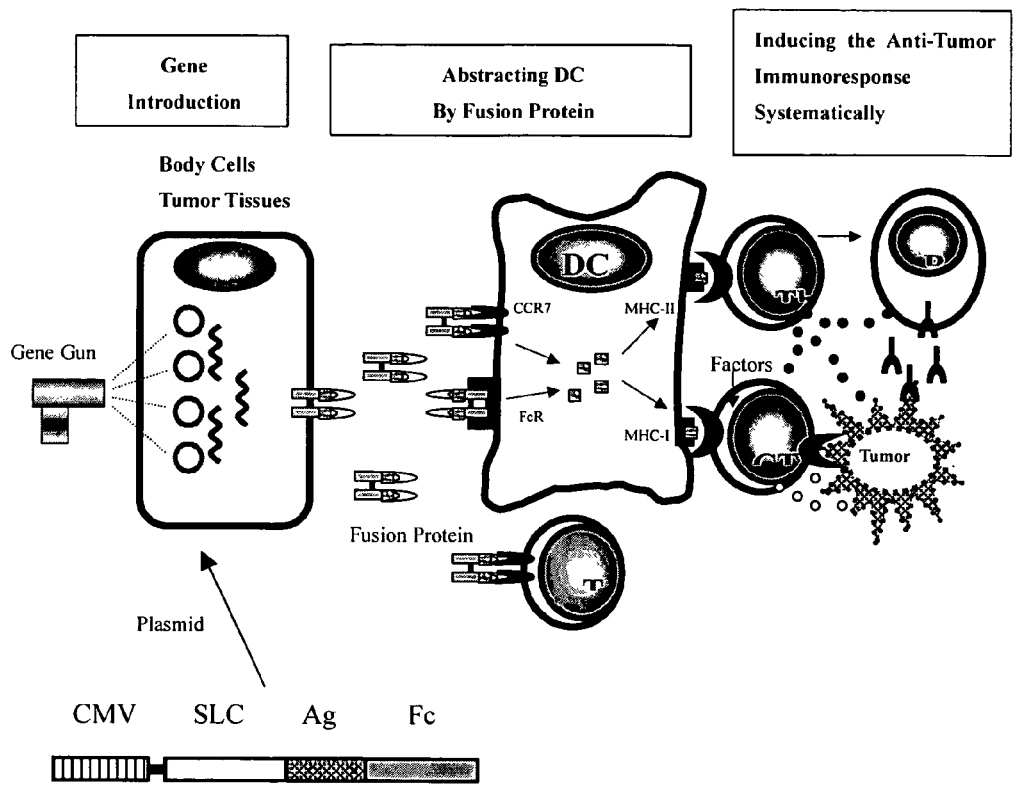
FIG. 1 shows a scheme for the mechanism of the chemotactic antigen gene vaccine of the present invention.

The invention will be described in details with the illustration of the invention. It should be apprehended that the aim of the relating embodiments is only to give an explanation, but not intending to restrict the invention.

Example

Cloning of Human SLC Gene

The mRNA was extracted from the lymph node of patients suffering from cancer. By using the methods well known for those skilled in the art, the KpnI restrictive endonuclease site was added to the SLC forward primer (5'-c ggtaccacagacatggctcagtcac-3') (SEQ ID NO: 14) and the sequence encoding three glycins and EcoRI restrictive endonuclease site was added to the SLC reverse primer (5'-t gaattctcctcctcctggcccctttagg-3') (SEQ ID NO: 15). The SLC gene was acquired by RT-PCR amplification. The acquired fragment was purified and inserted into pUCmT vector (pUC-SLC) for sequencing. The result shows that the sequence of the acquired fragment was in accordance with the designed sequence (the underlined fragment).

In this invention, sequencing of the PCR products was performed by using 377 DNA sequencer (ABI company) by four-colored fluorescence terminator sequencing method based on SANGER dideoxynucleotide chain termination method. The sequence from position 36 to position 464 is the sequence of the cloned fragment of the invention (Refer to SEQ ID NO: 3).

Example 2

Preparation and Linkage of Her-2/neu Gene

First, two fragments of Her-2/neu gene were cloned by PCR method. The first fragment was acquired as follows: The used forward primer is 5'-a gaattcaagatctttgggagcctggcatttctgggctacctgctcatcgctca c-3' (SEQ ID NO: 16), having EcoRI restrictive endonuclease site, and the used reverse primer is 5'-gatgcccagcccttgca gggccagggcatagttgtc-3' (SEQ ID NO: 17). The plasmid containing extra cellular segment of neu gene was adopted as template and the fragment corresponding to amino acid sequence from position 82 to position 115 was amplified, wherein the amino acid V at position 103 was replaced by amino acid L. The second fragment was acquired as follows: the forward primer was 5'-ctgcaagggctgggcatc-3' (SEQ ID NO: 18), and the reverse primer having NcoI restrictive endonuclease site was 5'-tccatggcccggttggcagtgtggag-3' (SEQ ID NO: 19). The fragment corresponding to amino acid sequence from position 445 to position 499 was amplified.

The two PCR products were collected and linked together in a PCR system. Further, the resulted fragment was used as template, by using the forward primer of the first fragment and the reverse primer of the second fragment; a fusion gene with 294 bp in size was amplified. Then the resulted fusion gene was inserted into pUCmT vector (pUC-Her2P) and sequenced. The result indicates that the sequence of the obtained fusion gene is in accordance with the designed sequence (the underlined sequence).

The result is indicated in SEQ ID NO: 4, wherein the sequence from position 121 to position 465 is the sequence of the cloned fragment of the invention.

Example 3

Cloning of p53 Gene Segment

A 402 bp gene fragment encoding the amino acids from position 156 to position 289 in p53 protein was cloned from the plasmid containing the whole length of p53 gene. The primers used were as follows: forward primer with one NcoI restrictive endonuclease site was 5'-acc atg gcc atc tac aag cag tca cag cac atg ac-3' (SEQ ID NO: 20); reverse primer with one EcoRV restrictive endonuclease site was 5'-tga tat ctt tct tgc gga gat tct ctt c-3' (SEQ ID NO: 21). The obtained fragment was inserted into pUCmT vector (pUC-p53P) for sequencing. The result indicates that the sequence of the obtained fragment is in accordance with the expected sequence (the underlined segment).

The result is indicated in SEQ ID NO: 5, wherein the sequence from position 39 to position 445 is the sequence of the inventive fragment.

Example 4

Linkage of Her2/neu and p53 Fragments

Figure 3:
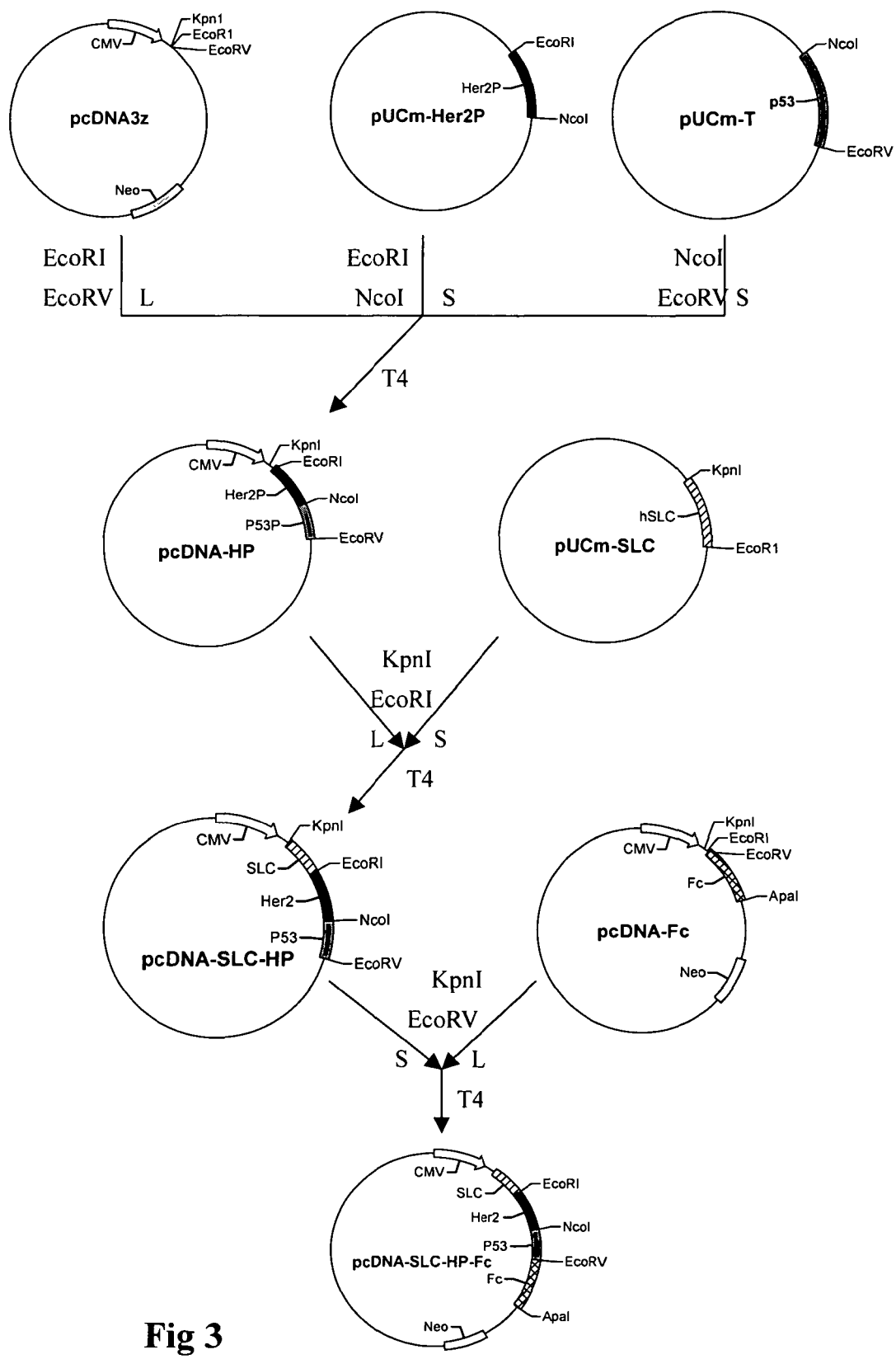
FIG. 3 shows the recombination of SLC-Her2/neu-Fc of the present invention.

As shown in FIG. 3, the smaller fragment cut from pUC-Her2P by EcoRI/NcoI and the smaller fragment cut from pUC-p53P by NcoI/EcoRV were ligated with the larger fragment cut from pcDNA3z by EcoRI/EcoRV to construct a plasmid of pcDNA-Her2/p53, also called pcDNA-HP. HP means a gene ligated by Her2/neu and p53. The artificially ligated Her2/neu-p53 fragment contains genes encoding HLA-I and HLA-II molecule-binding peptide.

Example 5

Construction of PcDNA-Fc

First, the chemically synthesized multiple cloning sites were used to replace the multiple cloning sites of pcDNA3.1.
The process of construction was as follows: Chemically synthesize two oligonucleotides.
The forward primer was 5'-GCTAGCGAAGCTTTGG-TACCGTAGGATCCACGAATTCAGTCCA GGATATCGGCGGTGG-3' (SEQ ID NO: 22)
The reverse primer was 5'-GGTTTAAACGTTAAC-CCCGGGCCCTCGAGCTCTAGAGCCTCCT CCACCGCCGATATC-3' (SEQ ID NO: 23)
The last 15 bases at the 3' ends of each primer are complementary to each other. The PCR product was obtained in a system with the mixture of the two primers at the ratio of 1:1, Taq DNA polymerase and dNTP at 45° C. for renaturing and elongation. The purified product was inserted into pUCmT vector for sequencing. The result shows that the sequence of the obtained product is in accordance with the designed sequence. The underlined sequence indicates the synthesized multiple cloning sites. The final resulting multiple cloning sites were: "NheI-HindIII-Kpn1-BamH1-EcoR1-EcoRV-Glysine×5-XbaI-Xho1-Apa1-Sma1-Hpa1-Pme1" ("Glysine× 5" disclosed as SEQ ID NO: 24). In this sequence, a small gene fragment (GGCGGTGGAGGAGGC) (SEQ ID NO: 25) encoding for five glycins (SEQ ID NO: 24) was inserted between EcoRV and XbaI sites. NheI/PmeI cut the cloned plasmid and a fragment about 100 bp in size was obtained. Then, the fragment was ligated with the larger fragment cut from pcDNA3. 1 by NheI/PmeI to construct a new vector named pcDNAf.
The result of sequencing the chemically synthesized multiple cloning site is indicated in SEQ ID NO: 6, wherein the sequence from position 3 to position 100 is the sequence of the inventive fragment.
The Process for Constructing PcDNA-Fc Plasmid
The Fc fragment was cut from IgG1 Fc-containing plasmid by XbaI/ApaI restrictive endonucleases and inserted into pcDNAf vector, wherein the pcDNAf vector was treated with the same endonuclease. The resulted construction was named as PcDNA-Fc. The sequence of IgG1 Fc was confirmed by sequencing the resulted plasmid.
The Sequencing of Fc Fragment
The Fc fragment with 900 bp in size was amplified from plasmid containing IgG1 Fc gene by PCR and inserted into pUCmT vector for sequencing. The primers used in the amplification were: forward primer: 5'-gaattcggagttaacgagc-ccaaatcttg-3' (SEQ ID NO: 26); reverse primer: 5'-gggcct-catttacccggagac-3' (SEQ ID NO: 27). The result of sequencing reveals that the plasmid contained the hinge region, CH2 and CH3 of IgG1. That is to say, the plasmid contained Fc fragment (See the underlined sequence). The result is indicated in SEQ ID NO: 7, wherein the sequence from position 78 to position 991 is the inventive sequence.

Example 6

Linkage of SLC-Her2/neu-Fc Gene

Figure 2:
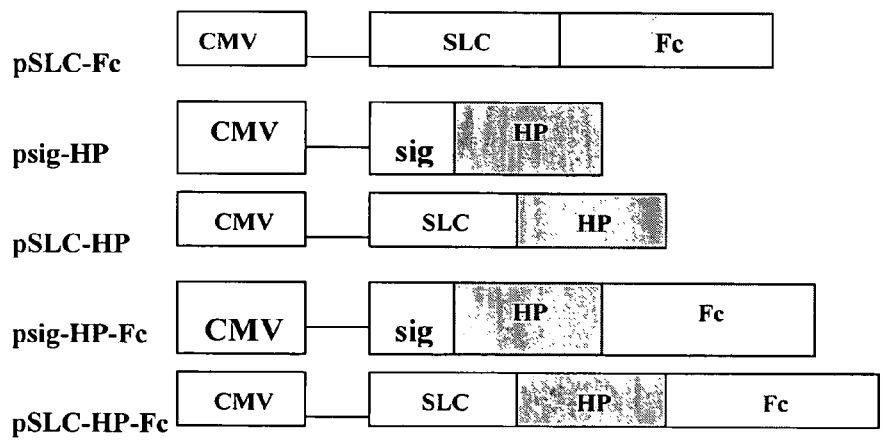
FIG. 2 shows the construction of the plasmids. HP indicates Her2/neu-p53 fusion gene; sig indicates SLC secreted peptide gene.

As shown in FIG. 3, the larger fragment cut from pcDNA-HP with KpnI/EcoRI was linked with the smaller fragment cut from pUC-SLC with KpnI/EcoRI to construct pcDNA-SLC-HP. Then, the smaller fragment cut from pcDNA-SLC-HP by KpnI/EcoRV was linked with the larger fragment cut from pcDNA-Fc by KpnI/EcoRV to construct pcDNA-SLC-HP-Fc (also named as pSLC-HP-Fc).
The construction of control plasmid is indicated in FIG. 2

Example 7

Figure 4:
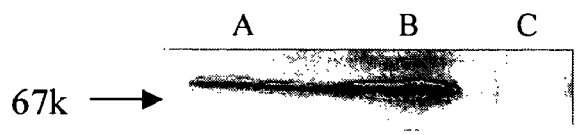
FIG. 4 shows the Western Blot detection for the cellular expression and secretion of fusion protein in the pSLC-HP-Fc gene vaccine transfected cells. A indicates pSLC-HP-Fc transfected cell lysates; B indicates the culture supernant from pSLC-HP-Fc transfected cells; C indicates the culture supernant from pcDNA transfected cells.

Detection of Cellular and Secreted Recombinant Protein in Cells Transfected with Gene Vaccine by Western Blot The recombinant plasmid of pSLC-HP-Fc was transfected into B16-F10 cells by using the method of liposome. The positive clones were selected by G418. Cultured the cells in serum-free 1640 medium for 24 hours, and then collected and concentrated the supernatant. The method of Western Blot was used to detect the expression of the fusion protein. The used primary antibody was rabbit-anti-human p53 polyclonal antibody, and the second antibody was HRP-conjugated goat-anti-rabbit antibody. The blots were visualized with ECL-Plus chemiluminescent detection kit (Amersham Pharmacia Biotech). Finally, the film was exposed to X-ray. The result indicates that the expression of fusion protein can be detected in the supernatant and cell lysate of B16-F10 cells transfected with pSLC-HP-Fc. The molecular weight is in accordance with what expected (See FIG. 4). It has been verified that the sequence of fusion protein is SEQ ID NO: 2.
Total RNA was extracted from human prostate cancer cell line LNCaP. RT-PCR was performed by using a forward primer (5'-ACTCGAGAT GAAGACATACAGTGTATC-3') (SEQ ID NO: 28) and a reverse primer (5'-TGATATCTTAG-GCTAC TTCACTCAAAG-3') (SEQ ID NO: 29). After electrophoresis, the hPSM band with 390 bp in size was cut out. The fragment was purified and recovered by the method of Glass Milk. The purified fragment was ligated with pUCm-T vector to construct pUCm-hPSM. The positive clone was picked up and sequenced. The result is in accordance with what is expected. Please refer to SEQ ID NO: 8, the obtained gene fragment is corresponding to the sequence from position 1864 to position 2253 in human PSM ORF. The sequence from position 229 to position 618 in the obtained sequence is the inventive sequence.

Example 9

Cloning of Human PSA (Prostate Specific Antigen) Gene Fragment

Total RNA was extracted from human prostate cancer cell line LNCaP. RT-PCR was performed by using a forward primer (5'-TCTCGAGGGC GGTGTTCTGGTGCA-3') (SEQ ID NO: 30) and a reverse primer (5'-AGATATCAT- GTCC AGCGTCCAGCAC-3') (SEQ ID NO: 31). After electrophoresis, the band with about 600 bp in size was cut out. The fragment was purified and recovered by the method of Glass Milk. The obtained fragment was inserted into pUCm-T to construct pUCm-PSA. The positive clone was picked up and sequenced. The result is indicated in SEQ ID NO: 9. The obtained gene fragment is corresponding to the sequence from position 151 to position 609 of human PSA ORF. The sequence from position 45 to position 503 in the obtained sequence is the inventive sequence.

Example 10

Cloning of Mouse PAP (Prostatic Acid Phosphatase) Gene Fragment

Total RNA was extracted from mouse prostate tissue. RT-PCR was performed by using a forward primer (5'-TCTA-GATGAGAGCTGTTCCTCTG-3') (SEQ ID NO: 32) and a reverse primer (5'-GGGCCCTTAATTCCGTCCTTGGTG-3') (SEQ ID NO: 33). After electrophoresis, the band with 1146 bp in size was cut out. The fragment was purified and recovered by the method of Glass Milk. The obtained fragment was inserted into pUCm-T to construct pUCm-mPAP. The positive clone was picked up and sequenced. The result is indicated in SEQ ID NO: 10. The sequence from position 48 to position 1193 in the obtained sequence is the inventive sequence.

Example 11

Linkage of PSM, mPAP, and PSA Gene Fragment (3P)

The hPSM gene fragment was cloned from pUCm-hPSM plasmid by PCR with the following primers: forward primer corresponding to the sequence from position 1987 to position 2007 of hPSM ORF (EcoRI restrictive endonuclease site was introduced) was 5'-AGAATTCATGATGAATGATCAACT-CATG-3' (SEQ ID NO: 34); reverse primer was 5'-AGCACTCATCAAAGTCCTGGCCTTGGAAGGGTCCAC-3' (SEQ ID NO: 35) (the underlined section was corresponding to the sequence from position 328 to position 345 of mPAP ORF, and the remains section was corresponding to the sequence from position 2155 to position 2172 of hPSM ORF). After electrophoresis, the obtained hPSM fragment was cut out and purified by the method of Glass Milk. The mPAP gene fragment was cloned from pUCm-mPAP plasmid by PCR with the following primers: forward primer corresponding to the sequence from position 328 to position 348 of mPAP ORF was 5'-AGGACTTTGATGAGTGCTATG-3' (SEQ ID NO: 36); the reverse primer corresponding to the sequence from position 463 to position 483 of mPAP ORF was 5'-AGGGCAGTCTCTGAAAGGCAG-3' (SEQ ID NO: 37). After electrophoresis, the obtained mPAP fragment was cut out and purified by the method of Glass Milk. The hPSA gene fragment was cloned from pUCm-hPSA plasmid by PCR with the following primers: the forward primer was 5'-CCTTTCAGAGACTGCCCTGGCGGTGTTC TGGT-CAC-3' (SEQ ID NO: 38) (the underlined section was corresponding to the sequence from position 466 to position 483 of mPAP ORF, and the remain section was corresponding to the sequence from position 151 to position 168 of hPSA ORF); the reverse primer was 5'-AGATATCGAGCAGCATGAG-GTCGT-3' (SEQ ID NO: 39). After electrophoresis, the obtained hPSA fragment was cut out and purified by the method of Glass Milk.

The primer of 5'-AGAATTCATGATGAATGATCAACT-CATG-3' (SEQ ID NO: 34) was used to amplify hPSM and the primer of 5'-AGGGCAGTCTCTGAAAGGCAG-3' (SEQ ID NO: 37) was used to amplify mPAP individually in a 25 μl system for 10 cycles to rich the single chains. Then, the two systems were mixed to further perform PCR in a 50 μl system for 18 cycles. After electrophoresis, the obtained hPSM-mPAP fragment with 352 bp in size was cut out and purified by the method of Glass Milk.

The primer of 5'-AGGACTTTGATGAGTGCTATG-3' (SEQ ID NO: 36) (corresponding to the sequence from position 328 to position 348 of mPAP ORF) was used to amplify mPAP and use the primer of 5'-AGATATCGAGCAGCAT-GAGGTCGTG-3' (SEQ ID NO: 40) (corresponding to the sequence from position 355 to position 372 of PSA ORF) to amplify hPSA individually in a 25 μl system for 10 cycles to rich the single chains. Then, the two systems were mixed to further perform PCR in the 50 μl system for 18 cycles. After electrophoresis, the obtained mPAP-hPSA fragment with 378 bp in size was cut out and purified by the method of Glass Milk.

The primer of 5'-AGAATTCATGATGAATGATCAACT-CATG-3' (SEQ ID NO: 34) was used to amplify hPSM-mPAP and the primer of 5'-AGATATCGAGCAGCATGAG-GTCGTG-3' (SEQ ID NO: 40) was used to amplify mPAP-hPSA individually in a 25 μl system for 10 cycles to rich the single chains. Then, the two systems were mixed to further perform PCR in the 50 μl system for 18 cycles. After electrophoresis, the obtained hPSM-mPAP-hPSA fragment with 564 bp in size was cut out and purified by the method of Glass Milk. The resulted fragment was inserted into pUCm-TV vector for sequencing. The result was in accordance with what was expected. See SEQ ID NO: 11, wherein the sequence from position 54 to position 629 is the inventive sequence.

Example 12

Recombination of Chemokine Antigen SLC-3P-Fc Gene

Figure 12:
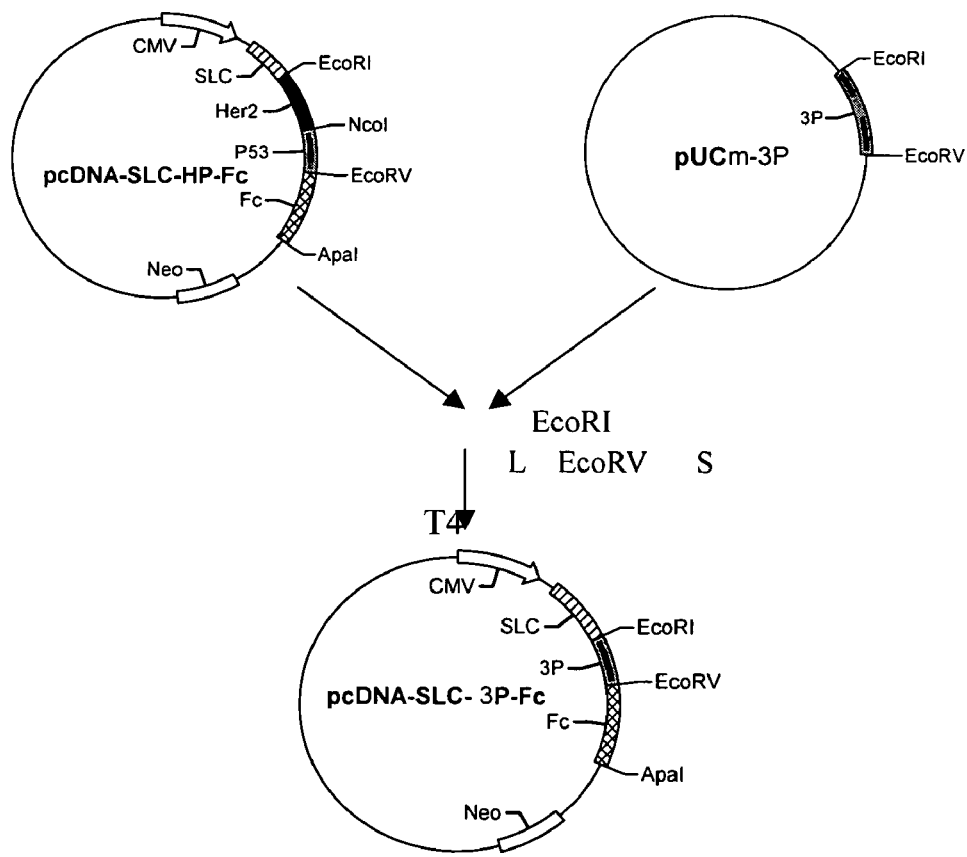
FIG. 12 shows the construction of the pSLC-3P-Fc plasmid.

After sequencing, the plasmid containing correct 3P gene sequence (3P means a PSM-PAP-PSA fusion gene with 564 bp in size encoding 188 amino acids) was cut by EcoRI/EcoRV restrictive endonucleases. The obtained smaller 3P fragment was ligated with EcoRI/EcoRV-cut pSLC-HP-Fc vector to construct pSLC-3P-Fc (See FIG. 12). The sequence of recombinant SLC-3P-Fc gene is shown in SEQ ID NO: 12, which is corresponding to amino acid sequence shown in SEQ ID NO: 13.

Tests Examples

Test 1. Detection of the Immune Cells-Chemoatactic Activity of Fusion Protein by Boyden Chamber In Vitro Abstracting Activity of Human SLC:
A. The Melanoma cell line B16F10 was transfected with the purified plasmid pcDNA3z-SLC-HP-Fc and the control plasmid. 48 hours after incubation, the culture medium was harvested and concentrated by PEG20000 (the supernant from untransfected B16-F10 cells was used as negative control).

B. Peripheral blood mononuclear cells (PBMC) were collected from the 5 ml of healthy whole peripheral blood by Lymphocyte Separation Medium, washed twice with saline, and re-suspended in RPMI-1640 serum-free medium. The PBMC were counted and diluted at the concentration of $1\times10^6$/ml.

C. Preparation of the Boyden Chamber: the Chamber was purchased from Neuro Probe Co. The lower wells of the chamber were filled with 27 μl conditioned culture medium, whereas the upper wells were filled with 50 μl of $1\times10^6$/ml PBMC cell suspension. The lower and upper wells were separated by a polycarbonate filter (Neuro Probe) with 5 μm pore size. The chamber was incubated at 37° C. with 5% $CO_2$ for 4 h.

D. The filter was unloaded and the cells were scraped off from the upper side of filter, following by washing, fixing and staining the filter. The migrated cells in five randomly selected high power (×200) fields were counted. The CI (Chemotactic Index) was calculated by the following: CI=the cell number of five high power field in the studied wells/cell number of five high power field in the control wells. The value of CI of negative group was 1.

TABLE 1

Detection of the chemoatactic activity of fusion protein

| Groups | Counts of chemoatactic cells | CI | P value |
|---|---|---|---|
| Negative control | 34 ± 10.4 | 1 | |
| Control vector | 44.6 ± 11.9 | 1.31 | >0.05* |
| psig-HP | 68.6 ± 9.5 | 2.02 | <0.05* |
| pSLC-HP-Fc | 157.4 ± 19.2 | 4.63 | <0.01* <0.05** |
| pSLC | 156.6 ± 20.3 | 4.61 | <0.01* <0.05** |

*vs negative control.
**vs psig-HP.

Result: The level of the chemotactic activity of serum-free supernant from cells transfected with pSLC-HP-Fc is significantly higher than others, indicating that after transfection, the plasmid can be expressed and the expressed protein has activity. The level of chemotactic ability of pSLC-HP-Fc transfecting cells is similar to that of pSLC transfecting cells, indicating that the fusion protein does affect the activity of SLC.

Test 2 Anti-Tumor Immune Response of Human Chemotactic Antigen Gene Vaccine in Mice The plasmids (nude gene) were loaded on gold particles and coated onto the inner surface of Tefzel tubing that was cut into proper segments as bullet to deliver 1 μg DNA according to the BioRad's manual. Several groups were divided as controls: control vector, pSLC-Fc, psig-HP (the plasmid expressing HP containing the SLC signal peptide), pSLC-HP and psig-HP-Fc.

Test 3 Immuno-Response Against Cancer 14 days and 7 days before tumor inoculation, the mice were vaccinated twice with pSLC-HP-Fc or control vectors at the abdomen skin. On day 0, each mouse was inoculated with $5\times10^4$ B16F10 tumor cells (The B16F10 cells were transfected with HP gene and selected by G418) in 0.2 ml solution. The tumor sizes were recorded 2-3 times per week. The tumor size was calculated as length (cm)×width ($cm^2$).

Figure 5:
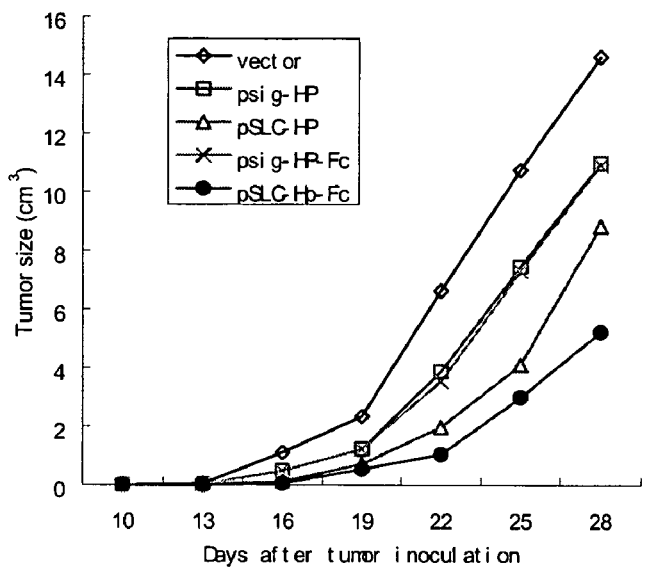
FIG. 5 shows the tumor-inhibiting effect in vivo by pre-vaccination of the tumor chemotactic antigen gene vaccine (pSLC-HP-Fc).
Figure 6:
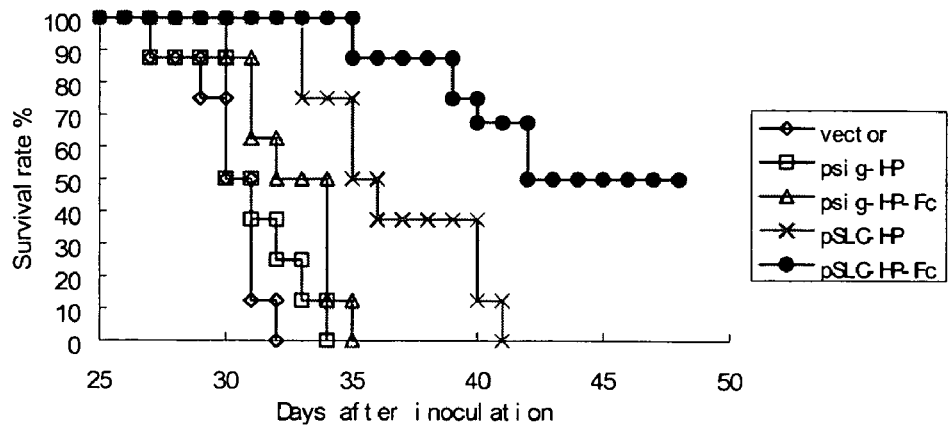
FIG. 6 shows the survival period of tumor-burden mice by pre-vaccination of the tumor chemotactic antigen gene vaccine (pSLC-HP-Fc).

Result: Vaccination of pSLC-HP-Fc twice significantly improves the tumor suppression effect (See FIG. 5, 6) and the average survival period of mice is significantly prolonged. The therapeutic effect of pSLC-HP-Fc is significantly better than any other vectors (p<0.05), indicating the synergistic immune effect of SLC and Fc fragments.

Test 4 Immunotherapy for Cancer

On day 0, the each mouse was inoculated with $5\times10^4$ B16F10 tumor cells in 0.2 ml solution. On day 6, 12, 18, the mice were vaccinated by Gene Gun System. The tumor sizes were recorded 2~3 times per week. The tumor sizes were evaluated as mentioned above.

Figure 7:
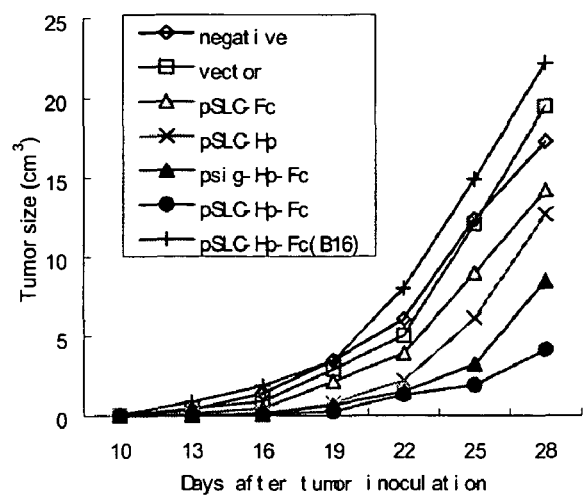
FIG. 7 shows the tumor-inhibiting effect in vivo by treatment of the tumor chemotactic antigen gene vaccine (pSLC-HP-Fc).
Figure 8:
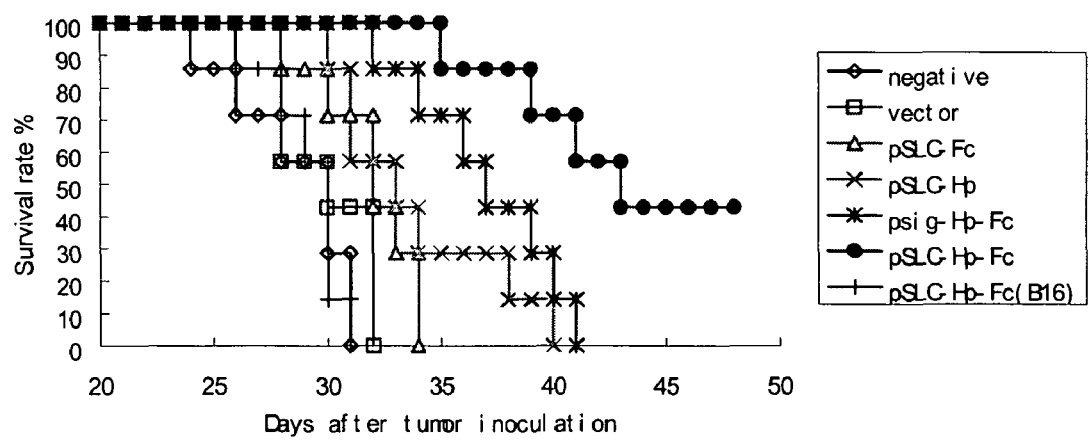
FIG. 8 shows the survival period by treatment of the tumor chemotactic antigen gene vaccine (pSLC-HP-Fc).

Result: As shown in FIGS. 7 and 8, the pSLC-HP-Fc vaccine displays the most effective suppression of tumor growth. On day 28, the difference between pSLC-HP-Fc and psig-HP-Fc groups is significant (P<0.05). The average survival period of mice is prolonged by pSLC-HP-Fc immunization. The mice in B16 (pSLC-HP-Fc) group are inoculated with wild type B16 cells. After three-time pSLC-HP-Fc immunization, the B16 group displays no tumor suppression effect, suggesting that pSLC-HP-Fc induced immune response is specific to HP antigen.

Test 5. CTL Activity Induced by the Tumor Chemotactic Antigen Gene Vaccine

Two weeks after three times of vaccination by Gene Gun System, tumor-bearing mice were killed and cytotoxicity assay of CTL was performed with the use of spleen cells by the LDH Kits (Promega). The ratio of spleen cell and target cell (E:T ratio) was 40:1, 20:1 and 10:1, respectively.

Figure 9:
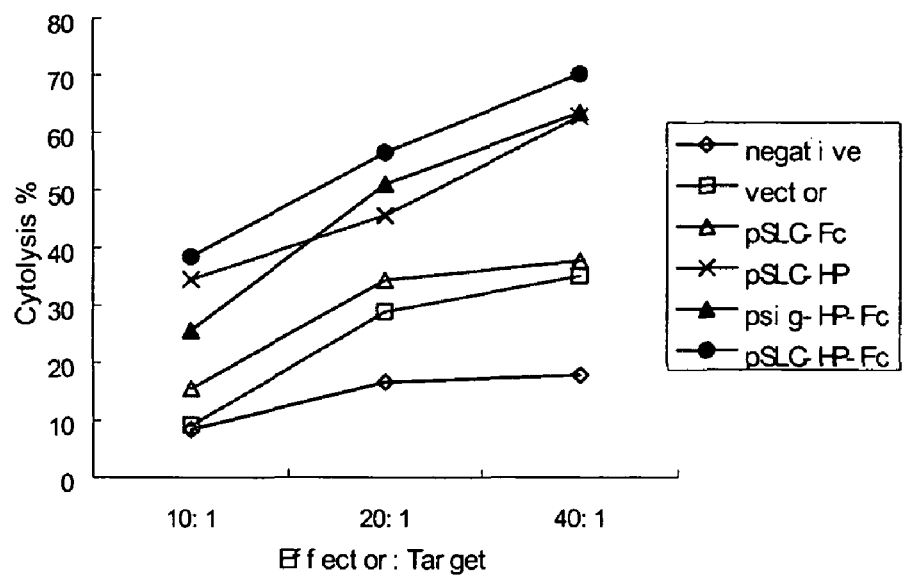
FIG. 9 shows the activity of CTL after immunization with the tumor chemotactic antigen gene vaccine (pSLC-HP-Fc).

Result: The lymphocytes derived from chemokine nucleotide vaccine immunized mice showed significant cytotoxicity effect on B16F10-HP cells (See FIG. 9). When the E:T ratios was 40:1 or 20:1, there was still significant difference between the studied vaccine and control vectors (P<0.05), suggesting that the vaccine was more powerful to induce CTL activity.

Test 6 Detection of Specific Antibodies in Serum of the Immunized Mice

The amount HP-specific antibodies in the serum of the immunized mice group was detected by ELISA, 2 and 4 weeks after immunization (pSLC-HP-Fc). Briefly, microtitre plates coated with recombinant p53 proteins were incubated overnight, blocked with 20% Calf Serum, and incubated with primary antibody (serially diluted mouse serum) and secondary antibody (horseradish peroxidase-conjugated goat anti-mouse IgG) in turn. After washing and visualizing by OPD (O-Phenylene diamine), the OD value was read at 490 nm. A monoclonal antibody against p53 was used as a positive control and normal mouse serum was used as a negative control.

Figure 10:
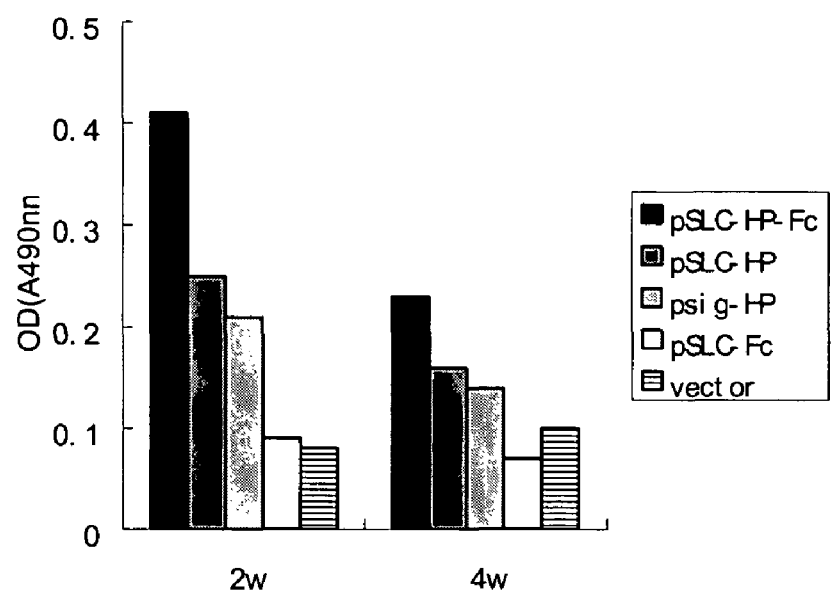
FIG. 10 shows the amounts of specific anti-HP antibody in the serum 2 and 4 weeks after vaccination. The mice serum is diluted at 1:100. ELISA assay is used.

Result: The level of p53 antibody of SLC-HP-Fc immunized mice is the highest and significantly higher than that of other vectors (See FIG. 10).

Test 7 pSLC-HP-Fc Immunization Induced Human Specific CTL Against Her2/neu or p53 In Vitro By centrifugation using Lymphocyte Separation Medium, mononuclear cells (MNCs) were collected from the whole peripheral blood of healthy HLA-A2+ donors. Half of the MNCs were transfected with the plasmid pSLC-HP-Fc using liposome and incubated with untreated MNCs at the ratio of 1:1 at 37□ with 5% CO2. On day 6, the viable cells were counted, re-suspended and cultured with different target cells at different E:T ratios in 96-well microplates. The LDH assay (Promega Kits) was used to analyze the cytotoxicity.

Figure 11:
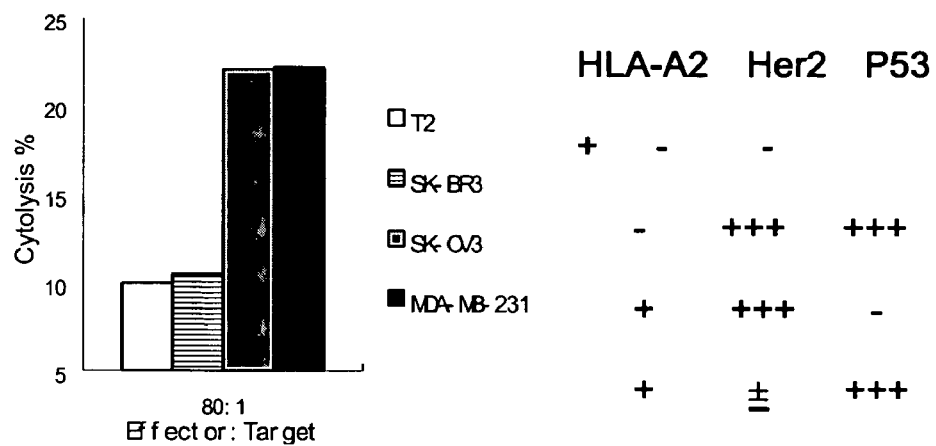
FIG. 11 shows that the pSLC-HP-Fc vaccine can induce CTL specifically against Her2/neu and p53 in vitro.

Result: After mixed culture, the pSLC-HP-Fc transfects MNC induced specific CTL to kill tumor cells that overexpress Her2/neu or p53 in a MHC-restricted manner (See FIG. 11). That is to say, the specific CTL only significantly kills HLA-A2+ tumor cells that express Her2/neu or p53, indicating the specificity of CTL induced by the chemotactic antigen gene vaccine.

Test 8 Anti-Prostate Cancer Effect of pSLC-3P-Fc Chemokine Antigen Gene Vaccine In Vivo $5 \times 10^4$ B16-3P cancer cells (pcDNA-3P transfected B16 cancer cells by G418 selection) were inoculated on the flank of C57BL/6 mice (eight mice each group). The mice were immunized on third, eighth and thirteen day after tumor cell inoculation. The control vector, pSLC-Fc, psig-3P (the plasmid containing with a SLC signal peptide gene upstream to 3P gene) were used as control groups. The tumor sizes and survival periods of mice were observed.

Figure 13:
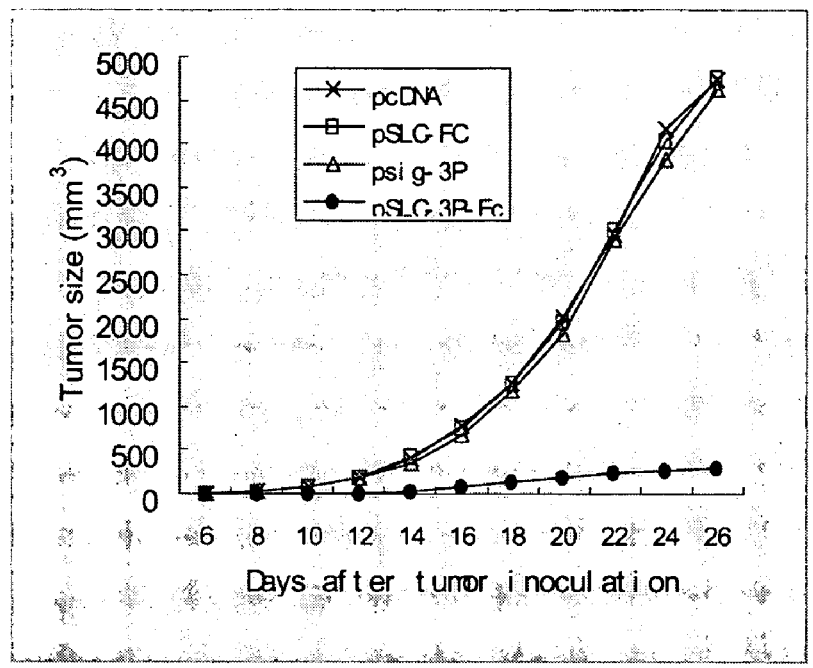
FIG. 13 shows the tumor-inhibiting effect in vivo after the treatment of the tumor chemotactic antigen gene vaccine (pSLC-3P-Fc).
Figure 14:
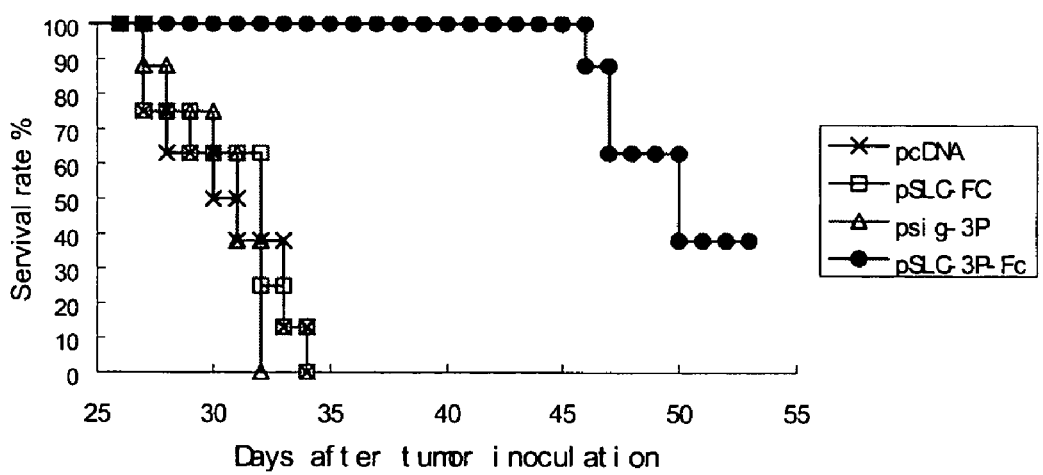
FIG. 14 shows the survival period after the treatment of the tumor chemotactic antigen gene vaccine (pSLC-3P-Fc).
Figure 15:
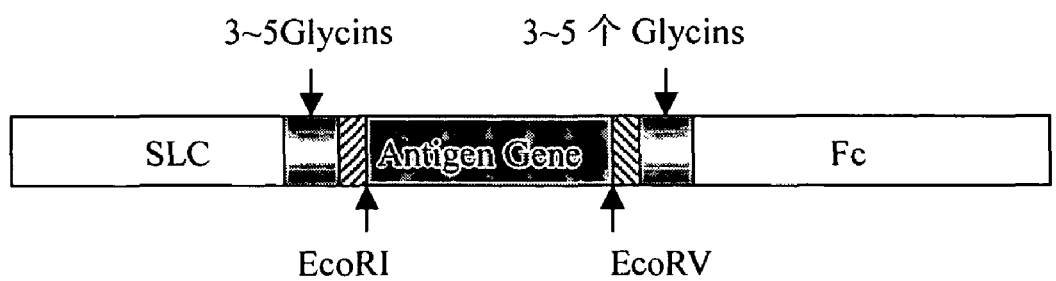
FIG. 15 shows the characteristic structure of the recombinant gene of the invention.

Result: As shown in FIGS. 13 and 14, the chemokine antigen gene vaccine (pSLC-3P-Fc) significantly inhibits the tumor growth (vs control groups P<0.05), and significantly prolongs the survival period (vs control groups P<0.05), suggesting change of the antigen in the chemotactic antigen gene vaccine can produce different vaccine against the associated antigen.

What is claimed is:

1. A recombinant nucleic acid comprising a human secondary lymphoid tissue chemokine (SLC) gene, an antigen gene, and an IgG1-Fc fragment gene, wherein the SLC gene is linked upstream to the antigen gene, and the IgG1-Fc fragment gene is linked downstream to the antigen gene, wherein an *E. coli* RI (EcoRI) restrictive endonuclease site and nucleic acid residues encoding three glycine residues are present between the SLC gene and the antigen gene, and an *E. coli* RV (EcoRV) restrictive endonuclease site and nucleic acid residues encoding five glycine residues are present between the antigen gene and the IgG1-Fc fragment gene.

2. The nucleic acid according to claim 1, wherein the antigen gene is selected from the group consisting of Her2/neu, p53, prostate specific antigen (PSA), prostatic acid phosphatase (PAP), prostate specific membrane antigen (PSM), MAGE1, MAGE2, MAGE3, BAGE, GAGE1, GAGE 2, CAG3, RAGE, NY-ESO-1, Tyrosinase, CEA, Ig idiotype, gp100, melan A, gp75, TRP-1, TRP-2, CDK4, CASP-8, ras, bcr/abl, and MUC-1.

3. The nucleic acid according to claim 1, wherein the nucleic acid has the sequence of SEQ ID NO: 1.

4. The nucleic acid according to claim 1, wherein the nucleic acid has the sequence of SEQ ID NO: 12.

5. A polypeptide having the amino acid sequence encoded by the nucleic acid sequence set forth in SEQ ID NO: 1.

6. The polypeptide according to claim 5, wherein the amino acid sequence is set forth in SEQ ID NO: 2.

7. A polypeptide having the amino acid sequence set forth in SEQ ID NO:13.

8. An anti-tumor gene vaccine comprising the nucleic acid according to claim 1 wherein the antigen gene is selected from the group consisting of Her2/neu, p53, prostate specific antigen (PSA), prostatic acid phosphatase (PAP), and prostate specific membrane antigen (PSM).

9. The gene vaccine according to claim 8, wherein the nucleic acid has the sequence set forth in SEQ ID NO: 1 or SEQ ID NO:12.

* * * * *

SEQUENCE LISTING

<160> NUMBER OF SEQ ID NOS: 41

<210> SEQ ID NO 1
<211> LENGTH: 2060
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atggctcagt cactggctct gagcctcctt atcctggttc tggcctttgg catccccagg      60
acccaaggca gtgatggagg ggctcaggac tgttgcctca agtacagcca aaggaagatt     120
cccgccaagg ttgtccgcag ctaccggaag caggaaccaa gcttaggctg ctccatccca     180
gctatcctgt tcttgccccg caagcgctct caggcagagc tatgtgcaga cccaaaggag     240
ctctgggtgc agcagctgat gcagcatctg gacaagacac catccccaca gaaaccagcc     300
cagggctgca ggaaggacag gggggcctcc aagactggca agaaaggaaa gggctccaaa     360
ggctgcaaga ggactgagcg gtcacagacc cctaaagggc caggaggagg agaattcaag     420
atctttggga gcctggcatt tctggctac ctgctcatcg ctcacaacca agtgaggcag       480
gtcccactgc agaggctgcg gattgtgcga ggcacccagc tctttgagga caactatgcc     540 ctggcctgc aagggctggg catcagctgg ctggggctgc gctcactgag ggaactgggc     600
agtggactgg ccctcatcca ccataacacc cacctctgct tcgtgcacac ggtgccctgg     660
gaccagctct ttcggaaccc gcaccaagct ctgctccaca ctgccaaccg ggccatggcc     720
atctacaagc agtcacagca catgacgaag gttgtgaggc gctgccccca ccatgagcgc     780
tgctcagata gcgatggtct ggccctcct cagcatctta tccgagtgga aggaaatttg     840
cgtgtggagt atttggatga cagaaacact tttcgacata gtgtggtggt gccctatgag     900
ccgcctgagg ttggctctga ctgtaccacc atccactaca actacatgtg taacagttcc     960
tgcatgggcg gcatgaaccg gaggcccatc ctcaccatca tcactggagt agactccagt    1020
ggtaatctac tgggacggaa cagctttgag gtgcgtgttt gtgcctgtcc tgggagagac    1080
cggcgcacag aggaagagaa tctccgcaag aaagatatcg gcgtggagg aggctctaga    1140 gtcgacgagc ccaaatcttg tgacaaaact cacacatgcc caccgtgccc aggtaagcca    1200
gcccaggcct cgccctccag ctcaaggcgg gacaggtgcc ctagagtagc ctgcatccaa    1260
ggacaggccc cagccgggtg ctgacacgtc cacctccatc tcttcctcag cacctgaact    1320 cctggggga ccgtcagtct tcctcttccc cccaaaaccc aaggacaccc tcatgatctc    1380
ccggacccct gaggtcacat gcgtggtggt ggacgtgagc cacgaagacc ctgaggtcaa    1440
```

```
gttcaactgg tacgtggacg gcgtggaggt gcataatgcc aagacaaagc cgcgggagga   1500 gcagtcaac  agcacgtacc gtgtggtcag cgtcctcacc gtcctgcacc aggactggct   1560
gaatggcaag gagtacaagt gcaaggtctc caacaaagcc ctcccagccc ccatcgagaa   1620
aaccatctcc aaagccaaag gtgggacccg tggggtgcga gggccacatg acagaggcc    1680 ggctcggccc accctctgcc ctgagagtga ccgctgtacc aacctctgtc cctacagggc   1740
agccccgaga accacaggtg tacaccctgc cccatcccg  ggatgagctg accaagaacc   1800
aggtcagcct gacctgcctg gtcaaaggct tctatcccag cgacatcgcc gtggagtggg   1860
agagcaatgg gcagccggag aacaactaca agaccacgcc tcccgtgctg gactccgacg   1920
gctccttctt cctctacagc aagctcaccg tggacaagag caggtggcag caggggaacg   1980
tcttctcatg ctccgtgatg catgaggctc tgcacaacca ctacacgcag aagagcctct   2040
ccctgtctcc gggtaaatga                                               2060

<210> SEQ ID NO 2
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Gln Ser Leu Ala Leu Ser Leu Leu Ile Leu Val Leu Ala Phe
1               5                   10                  15

Gly Ile Pro Arg Thr Gln Gly Ser Asp Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro Gly Gly Glu Phe Lys Ile Phe Gly Ser
    130                 135                 140

Leu Ala Phe Leu Gly Tyr Leu Leu Ile Ala His Asn Gln Val Arg Gln
145                 150                 155                 160

Val Pro Leu Gln Arg Leu Arg Ile Val Arg Gly Thr Gln Leu Phe Glu
                165                 170                 175

Asp Asn Tyr Ala Leu Ala Leu Gln Gly Leu Gly Ile Ser Trp Leu Gly
            180                 185                 190

Leu Arg Ser Leu Arg Glu Leu Gly Ser Gly Leu Ala Leu Ile His His
        195                 200                 205

Asn Thr His Leu Cys Phe Val His Thr Val Pro Trp Asp Gln Leu Phe
    210                 215                 220

Arg Asn Pro His Gln Ala Leu Leu His Thr Ala Asn Arg Ala Met Ala
225                 230                 235                 240

Ile Tyr Lys Gln Ser Gln His Met Thr Glu Val Val Arg Cys Pro
                245                 250                 255
```

```
His His Glu Arg Cys Ser Asp Ser Asp Gly Leu Ala Pro Pro Gln His
            260                 265                 270

Leu Ile Arg Val Glu Gly Asn Leu Arg Val Glu Tyr Leu Asp Asp Arg
            275                 280                 285

Asn Thr Phe Arg His Ser Val Val Pro Tyr Glu Pro Pro Glu Val
            290                 295                 300

Gly Ser Asp Cys Thr Thr Ile His Tyr Asn Tyr Met Cys Asn Ser Ser
305                 310                 315                 320

Cys Met Gly Gly Met Asn Arg Arg Pro Ile Leu Thr Ile Ile Thr Leu
                325                 330                 335

Glu Asp Ser Ser Gly Asn Leu Leu Gly Arg Asn Ser Phe Glu Val Arg
            340                 345                 350

Val Cys Ala Cys Pro Gly Arg Asp Arg Arg Thr Glu Glu Glu Asn Leu
            355                 360                 365

Arg Lys Lys Asp Ile Gly Gly Gly Gly Ser Arg Val Asp Glu Pro
370                 375                 380

Lys Ser Cys Asp Lys Thr His Thr Cys Pro Pro Cys Ala Pro Glu Leu
385                 390                 395                 400

Leu Gly Gly Pro Ser Val Phe Leu Phe Pro Pro Lys Pro Lys Asp Thr
                405                 410                 415

Leu Met Ile Ser Arg Thr Pro Glu Val Thr Cys Val Val Val Asp Val
            420                 425                 430

Ser His Glu Asp Pro Glu Val Lys Phe Asn Trp Tyr Val Asp Gly Val
            435                 440                 445

Glu Val His Asn Ala Lys Thr Lys Pro Arg Glu Glu Gln Tyr Asn Ser
450                 455                 460

Thr Tyr Arg Val Val Ser Val Leu Thr Val Leu His Gln Asp Trp Leu
465                 470                 475                 480

Asn Gly Lys Glu Tyr Lys Cys Lys Val Ser Asn Lys Ala Leu Pro Ala
                485                 490                 495

Pro Ile Glu Lys Thr Ile Ser Lys Ala Lys Gln Pro Arg Glu Pro Gln
            500                 505                 510

Val Tyr Thr Leu Pro Pro Ser Arg Asp Glu Leu Thr Lys Asn Gln Val
            515                 520                 525

Ser Leu Thr Cys Leu Val Lys Gly Phe Tyr Pro Ser Asp Ile Ala Val
530                 535                 540

Glu Trp Glu Ser Asn Gly Gln Pro Glu Asn Asn Tyr Lys Thr Thr Pro
545                 550                 555                 560

Pro Val Leu Asp Ser Asp Gly Ser Phe Phe Leu Tyr Ser Lys Leu Thr
                565                 570                 575

Val Asp Lys Ser Arg Trp Gln Gln Gly Asn Val Phe Ser Cys Ser Val
            580                 585                 590

Met His Glu Ala Leu His Asn His Tyr Thr Gln Lys Ser Leu Ser Leu
            595                 600                 605

Ser Pro Gly Lys
        610

<210> SEQ ID NO 3
<211> LENGTH: 512
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
atatcccatg gcggccgcc tgcagaccag gtctcggtac cacagacatg gctcagtcac      60
tggctctgag cctccttatc ctggttctgg cctttggcat ccccaggacc caaggcagtg     120 atggagggc tcaggactgt tgcctcaagt acagccaaag gaagattccc gccaaggttg     180
tccgcagcta ccggaagcag gaaccaagct taggctgctc catcccagct atcctgttct     240
tgccccgcaa gcgctctcag gcagagctat gtgcagaccc aaaggagctc tgggtgcagc     300
agctgatgca gcatctggac aagacaccat ccccacagaa accagcccag ggctgcagga     360
aggacagggg ggcctccaag actggcaaga aggaaaggg ctccaaaggc tgcaagagga     420
ctgagcggtc acagacccct aaagggccag gaggaggaga attcaaagac tggagatctg     480
gatccctcga gtctagagtc gacctgcagg ca                                   512
```

<210> SEQ ID NO 4
<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gtgagttagc tcactcatta ggcaccccag gctttacact ttatgcttcc ggctcgtatg      60
ttgtgtggaa ttgtgagcgg ataacaattt cacacaggaa acagctatga ccatgattac     120
gaattcgagc tcggtacccg gggatcctct agagattaga attcaagatc tttgggagcc     180
tggcatttct gggctacctg ctcatcgctc acaaccaagt gaggcaggtc ccactgcaga     240
ggctgcggat tgtgcgaggc acccagctct ttgaggacaa ctatgccctg gctctgcaag     300
ggctgggcat cagctggctg gggctgcgct cactgaggga actgggcagt ggactggccc     360
tcatccacca taaacacccac ctctgcttcg tgcacacggt gccctgggac cagctctttc     420
ggaacccgca ccaagctctg ctccacactg ccaaccgggc catggaaatc gtcgacctgc     480
aggcatgcaa gcttggca                                                   498
```

<210> SEQ ID NO 5
<211> LENGTH: 721
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gccagtgcca agcttgcatg cctgcaggtc gacgattacc atggccatct acaagcagtc      60
acagcacatg acggaggttg tgaggcgctg cccccaccat gagcgctgct cagatagcga     120
tggtctggcc cctcctcagc atcttatccg agtggaagga aatttgcgtg tggagtattt     180
ggatgacaga aacactttc gacatagtgt ggtggtgccc tatgagccgc tgaggttgg     240 ctctgactgt accaccatcc actacaacta catgtgtaac agttcctgca tgggcggcat     300
gaaccggagg cccatcctca ccatcatcac actggaagac tccagtggta atctactggg     360
acggaacagc tttggggtgc gtgtttgtgc ctgtcctggg agagaccggc gcacagagga     420
agagaatctc cgcaagaaag atatcaaatc tctagaggat ccccgggtac cgagctcgaa     480
ttcgtaatca tggtcatagc tgtttcctgt gtgaaattgt tatccgctca caattccaca     540
caacatacga gccggaagca taaagtgtaa agcctggggt gcctaatgag tgagctaact     600
cacattaatt gcgttgcgct cactgcccgc ttccagtcgg gaaacctgtc gtgccagctg     660
```

```
cattaatgaa tcggccaacg cgcggggaga ggcggtttgc gtattgggcg ctcttccgct    720
t                                                                   721

<210> SEQ ID NO 6
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
tggctagcga agctttggta ccgtaggatc cacgaattca gtccaggata tcggcggtgg     60
aggaggctct agagctcgag ggcccggggt taacgtttaa acccgctgat cagcctcgac    120
tgtgccttct agttgccagc catctgttgt ttgcccctcc cccgtgcctt ccttgaccct    180
ggaaggtgcc actcccactg tcctttccta ataaaatgag gaaattgcat cgcattgtct    240
gagtaggtgt cattctattc tggggggtgg ggtggggcag acagcaagg gggaggattg    300 ggaagacaat agcaggcatg ctggggatgc ggtgg                              335

<210> SEQ ID NO 7
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tatgccaagc ttgcatgcct gcaggtcgac tctagactcg aggatccag atctccagtc     60 ttgaattcgg agttaacgag cccaaatctt gtgacaaaac tcacacatgc ccaccgtgcc    120
caggtaagcc agcccaggcc tcgcctcca gctcaaggcg ggacaggtgc cctagagtag    180
cctgcatcca gggacaggcc cagccgggt gctgacacgt ccacctccat ctcttcctca    240
gcacctgaac tcctgggggg accgtcagtc ttcctcttcc cccaaaaacc caaggacacc    300
ctcatgatct cccggacccc tgaggtcaca tgcgtggtgg tggacgtgag ccacgaagac    360
cctgaggtca agttcaactg gtacgtggac ggcgtggagg tgcataatgc caagacaaag    420
ccgcgggagg agcagtacaa cagcacgtac cgtgtggtca gcgtcctcac cgtcctgcac    480
caggactggc tgaatggcaa ggagtacaag tgcaaggtct ccaacaaagc cctcccagcc    540
cccatcgaga aaaccatctc caaagccaaa ggtgggaccc gtggggtgcg agggccacat    600
ggacagaggc cggctcggcc caccctctgc cctgagagtg accgctgtac caacctctgt    660
ccctacaggg cagccccgag aaccacaggt gtacaccctg cccccatccc gggatgagct    720
gaccaagaac caggtcagcc tgacctgcct ggtcaaaggc ttctatccca gcgacatcgc    780
cgtggagtgg gagagcaatg ggcagccgga gaacaactac aagaccacgc ctcccgtgct    840
ggactccgac ggctccttct tcctctacag caagctcacc gtggacaaga gcaggtggca    900
gcaggggaac gtcttctcat gctccgtgat gcatgaggct ctgcacaacc actacacgca    960
gaagagcctc tccctgtctc cgggtaaatg agggcccaga cctggtctgc aggcggccgc   1020
ccatgggata tcatcgatca tatgtcgccc tatagtgagt cgtattacgg taccgag      1077

<210> SEQ ID NO 8
<211> LENGTH: 651
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 8

```
tttcccgact ggaaagcggg cagtgagcgc aacgcaatta atgtgagtta gctcactcat      60
taggcacccc aggctttaca ctttatgctt ccggctcgta tgttgtgtgg aattgtgagc     120
ggataacaat ttcacacagg aaacagctat gaccatgatt acgccaagct tgcatgcctg     180
caggtcgact ctagactcga gggatccaga tctccagtct tactcgagat gaagacatac     240
agtgtatcat ttgattcact tttttctgca gtaaagaatt ttacagaaat tgcttccaag     300
ttcagtgaga gactccagga ctttgacaaa agcaacccaa tagtattaag aatgatgaat     360
gatcaactca tgtttctgga aagagcattt attgatccat tagggttacc agacaggcct     420
ttttataggc atgtcatcta tgctccaagc agccacaaca gtatgcagg ggagtcattc      480
ccaggaattt atgatgctct gtttgatatt gaaagcaaag tggacccttc caaggcctgg     540
ggagaagtga agagacagat ttatgttgca gccttcacag tgcaggcagc tgcagagact     600
ttgagtgaag tagcctaaga tatcaagacc tgatctgcag gcggccgccc a              651
```

<210> SEQ ID NO 9
<211> LENGTH: 643
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgatatccc atgggcggcc gcctgcagac caggtcttct cgagggcggt gttctggtgc      60
accccagtg gtcctcaca gctgcccact gcatcaggaa caaaagcgtg atcttgctgg      120
gtcggcacag cctgtttcat cctgaagaca caggccaggt atttcaggtc agccacagct     180
tcccacaccc gctctacgat atgagcctcc tgaagaatcg attcctcagg ccaggtgatg     240
actccagcca cgacctcatg ctgctccgcc tgtcagagcc tgccgagctc acggatgctg     300
tgaaggtcat ggacctgccc acccaggagc cagcactggg gaccacctgc tacgcctcag     360
gctggggcag cattgaacca gaggagttct tgacccaaa gaaacttcag tgtgtggacc      420
tccatgttat ttccaatgac gtgtgtgcgc aagttcaccc tcagaaggtg accaagttca     480
tgctgtgtgc tggacgctgg acatgatatc taagactgga gatctggatc cctcgagtct     540
agagtcgacc tgcaggcatg caagcttggc gtaatcatgg tcatagctgt ttcctgtgtg     600
aaattgttat ccgctcacaa ttccacacaa catacgaacc cgg                       643
```

<210> SEQ ID NO 10
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gatcgatgat atcccatggg cggccgcctg cagaccaggt cttctagatg agagctgttc      60
ctctgcccct gagcccgaca gcaagcctca gccttggctt cttgctcctg ctttctctct     120
gcctggaccc aggccaagcc aaggagttga agtttgtgac attggtgttt cgacatggag     180
accgaggtcc catcgagacc tttcctaccg accccattac ggaatcctcg tggccacaag     240
```

```
gatttggcca actcacccag tggggcatgg aacagcacta cgaacttgga agttatataa        300
ggaaaagata cggaagattc ttgaacgaca cctataagca tgatcagatt tatatccgga        360
gcacagatgt ggacaggact tgatgagtg ctatgacaaa ccttgcagcc ctgtttcctc         420
cagaggggat cagcatctgg aatcctagac tgctctggca gcccatccca gtgcacaccg        480
tgtctctctc tgaggatcgg ttgctgtacc tgcctttcag agactgccct cgttttgaag        540
aactcaagag tgagactta gaatctgagg aattcttgaa gaggcttcat ccatataaaa         600
gcttcctgga caccttgtcg tcgctgtcgg gattcgatga ccaggatctt tttggaatct        660
ggagtaaagt ttatgaccct ttattctgcg agagtgttca caatttcacc ttgccctcct        720
gggccaccga ggacgccatg attaagttga gagagctatc agaattatct ctgctatcac        780
tttatggaat tcacaagcag aaagagaaat ctcgactcca aggggcgtc ctggtcaatg         840 aaatcctcaa gaatatgaag cttgcaactc agccacagaa gtataaaaag ctggtcatgt        900
attccgcaca cgacactacc gtgagtggcc tgcagatggc gctagatgtt tataatggag        960
ttctgcctcc ctacgcttct tgccacatga tggaattgta ccatgataag ggggggcact       1020
ttgtggagat gtactatcgg aatgagaccc agaacgagcc ctaccactc acgctgccag        1080 gctgcaccca cagctgccct ctggagaagt ttgcggagct actggacccg tgatctccc         1140 aggactgggc cacggagtgt atggccacaa gcagccacca aggacggaat taagggccca       1200
agactggaga tctggatccc tcgagtctag agtcgacctg caggcatgca agcttgg          1257
```

<210> SEQ ID NO 11
<211> LENGTH: 652
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
cttgcatgcc tgcaggtcga ctctagactc gagggatcca gatctccagt ctagaattca         60
tgatgaatga tcaactcatg tttctggaaa gagcatttat tgatccatta gggttaccag        120
acaggccttt ttataggcat gtcatctatg ctccaagcag ccacaacaag tatgcagggg        180
agtcattccc aggaatttat gatgctctgt tgatattga aagcaaagtg gacccttcca        240
aggccaggac tttgatgagt gctatgacaa accttgcagc cctgtttcct ccagagggga        300
tcagcatctg gaatcctaga ctgctctggc agcccatccc agtgcacacc gtgtctctct        360
ctgaggatcg gttgctgtac ctgcctttca gagactgccc tggcggtgtt ctggtgcacc        420
cccagtgggt cctcacagct gcccactgca tcaggaacaa aagcgtgatc ttgctgggtc        480
ggcacagcct gtttcatcct gaagacacag gccaggtatt tcaggtcagc cacagcttcc        540
cacacccgct ctacgatatg agcctcctga gaatcgatt cctcaggcca ggtgatgact        600
ccagccacga cctcatgctg ctcgatatct aaacctggtc tgcaggcggc cg               652
```

<210> SEQ ID NO 12
<211> LENGTH: 1928
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atggctcagt cactggctct gagcctcctt atcctggttc tggcctttgg catccccagg         60
```

```
acccaaggca gtgatggagg ggctcaggac tgttgcctca agtacagcca aaggaagatt    120
cccgccaagg ttgtccgcag ctaccggaag caggaaccaa gcttaggctg ctccatccca    180
gctatcctgt tcttgccccg caagcgctct caggcagagc tatgtgcaga cccaaaggag    240
ctctgggtgc agcagctgat gcagcatctg acaagacac catccccaca gaaaccagcc    300
cagggctgca ggaaggacag gggggcctcc aagactggca gaaaggaaa gggctccaaa    360
ggctgcaaga ggactgagcg gtcacagacc cctaaagggc caggaggagg agaattcatg    420
atgaatgatc aactcatgtt tctggaaaga gcatttattg atccattagg gttaccagac    480
aggccttttt ataggcatgt catctatgct ccaagcagcc acaacaagta tgcaggggag    540
tcattcccag gaatttatga tgctctgttt gatattgaaa gcaaagtgga cccttccaag    600
gccaggactt tgatgagtgc tatgacaaac cttgcagccc tgtttcctcc agaggggatc    660
agcatctgga atcctagact gctctggcag cccatcccag tgcacaccgt gtctctctct    720
gaggatcggt tgctgtacct gcctttcaga gactgccctg gcggtgttct ggtgcacccc    780
cagtgggtcc tcacagctgc ccactgcatc aggaacaaaa gcgtgatctt gctgggtcgg    840
cacagcctgt tcatcctga agacacaggc caggtatttc aggtcagcca agcttccca    900
cacccgctct acgatatgag cctcctgaag aatcgattcc tcaggccagg tgatgactcc    960
agccacgacc tcatgctgct cgatatcggc ggtggaggag gctctagagt cgacgagccc   1020
aaatcttgtg acaaaactca cacatgccca ccgtgcccag gtaagccagc ccaggcctcg   1080
ccctccagct caaggcggga caggtgcccc agagtagcct gcatccaggg acaggccca   1140
gccgggtgct gacacgtcca cctccatctc ttcctcagca cctgaactcc tggggggacc   1200
gtcagtcttc ctcttccccc caaaacccaa ggacaccctc atgatctccc ggacccctga   1260
ggtcacatgc gtggtggtgg acgtgagcca cgaagaccct gaggtcaagt tcaactggta   1320
cgtggacggc gtggaggtgc ataatgccaa gacaaagccg cgggaggagc agtacaacag   1380
cacgtaccgt gtggtcagcg tcctcaccgt cctgcaccag gactggctga atggcaagga   1440
gtacaagtgc aaggtctcca acaaagccct cccagccccc atcgagaaaa ccatctccaa   1500
agccaaaggt gggacccgtg gggtgcgagg gccacatgga cagaggccgg ctcggcccac   1560
cctctgccct gagagtgacc gctgtaccaa cctctgtccc tacagggcag ccccgagaac   1620
cacaggtgta caccctgccc ccatcccggg atgagctgac caagaaccag gtcagcctga   1680
cctgcctggt caaaggcttc tatcccagcg acatcgccgt ggagtgggag agcaatgggc   1740
agccggagaa caactacaag accacgcctc ccgtgctgga ctccgacggc tccttcttcc   1800
tctacagcaa gctcaccgtg gacaagagca ggtggcagca ggggaacgtc ttctcatgct   1860
ccgtgatgca tgaggctctg cacaaccact acacgcagaa gagcctctcc ctgtctccgg   1920
gtaaatga                                                            1928
```

<210> SEQ ID NO 13
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

```
Leu Lys Tyr Ser Gln Arg Lys Ile Pro Ala Lys Val Val Arg Ser Tyr
        35                  40                  45
Arg Lys Gln Glu Pro Ser Leu Gly Cys Ser Ile Pro Ala Ile Leu Phe
 50                  55                  60
Leu Pro Arg Lys Arg Ser Gln Ala Glu Leu Cys Ala Asp Pro Lys Glu
 65                  70                  75                  80
Leu Trp Val Gln Gln Leu Met Gln His Leu Asp Lys Thr Pro Ser Pro
                     85                  90                  95
Gln Lys Pro Ala Gln Gly Cys Arg Lys Asp Arg Gly Ala Ser Lys Thr
                100                 105                 110
Gly Lys Lys Gly Lys Gly Ser Lys Gly Cys Lys Arg Thr Glu Arg Ser
                115                 120                 125
Gln Thr Pro Lys Gly Pro Gly Gly Glu Phe Met Met Asn Asp Gln
                130                 135                 140
Leu Met Phe Leu Glu Arg Ala Phe Ile Asp Pro Leu Gly Leu Pro Asp
145                 150                 155                 160
Arg Pro Phe Tyr Arg His Val Ile Tyr Ala Pro Ser Ser His Asn Lys
                165                 170                 175
Tyr Ala Gly Glu Ser Phe Pro Gly Ile Tyr Asp Ala Leu Phe Asp Ile
                180                 185                 190
Glu Ser Lys Val Asp Pro Ser Lys Ala Arg Thr Leu Met Ser Ala Met
                195                 200                 205
Thr Asn Leu Ala Ala Leu Phe Pro Pro Glu Gly Ile Ser Ile Trp Asn
            210                 215                 220
Pro Arg Leu Leu Trp Gln Pro Ile Pro Val His Thr Val Ser Leu Ser
225                 230                 235                 240
Glu Asp Arg Leu Leu Tyr Leu Pro Phe Arg Asp Cys Pro Gly Gly Val
                245                 250                 255
Leu Val His Pro Gln Trp Val Leu Thr Ala Ala His Cys Ile Arg Asn
                260                 265                 270
Lys Ser Val Ile Leu Leu Gly Arg His Ser Leu Phe His Pro Glu Asp
                275                 280                 285
Thr Gly Gln Val Phe Gln Val Ser His Ser Phe Pro His Pro Leu Tyr
                290                 295                 300
Asp Met Ser Leu Leu Lys Asn Arg Phe Leu Arg Pro Gly Asp Asp Ser
305                 310                 315                 320
Ser His Asp Leu Met Leu Leu Asp Ile Gly Gly Gly Gly Ser Arg
            325                 330                 335
Val Asp Glu Pro Lys Ser Cys Asp Lys Thr His Thr Cys Pro Pro Cys
                340                 345                 350
Ala Pro Glu Leu Leu Gly Gly Pro Ser Val Phe Leu Phe Pro Pro Lys
                355                 360                 365
Pro Lys Asp Thr Leu Met Ile Ser Arg Thr Pro Glu Val Thr Cys Val
            370                 375                 380
Val Val Asp Val Ser His Glu Asp Pro Glu Val Lys Phe Asn Trp Tyr
385                 390                 395                 400
Val Asp Gly Val Glu Val His Asn Ala Lys Thr Lys Pro Arg Glu Glu
                405                 410                 415
Gln Tyr Asn Ser Thr Tyr Arg Val Val Ser Val Leu Thr Val Leu His
                420                 425                 430
Gln Asp Trp Leu Asn Gly Lys Glu Tyr Lys Cys Lys Val Ser Asn Lys
            435                 440                 445
Ala Leu Pro Ala Pro Ile Glu Lys Thr Ile Ser Lys Ala Lys Gln Pro
```

```
                450             455             460
Arg Glu Pro Gln Val Tyr Thr Leu Pro Pro Ser Arg Asp Glu Leu Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
                515                 520                 525

Ser Lys Leu Thr Val Asp Lys Ser Arg Trp Gln Gln Gly Asn Val Phe
            530                 535                 540

Ser Cys Ser Val Met His Glu Ala Leu His Asn His Tyr Thr Gln Lys
545                 550                 555                 560

Ser Leu Ser Leu Ser Pro Gly Lys
                565

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggtaccaca gacatggctc agtcac                                          26

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgaattctcc tcctcctggc cctttagg                                        28

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agaattcaag atctttggga gcctggcatt tctgggctac ctgctcatcg ctcac          55

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatgcccagc ccttgcaggg ccagggcata gttgtc                               36

<210> SEQ ID NO 18
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 18
ctgcaagggc tgggcatc                                                 18

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tccatggccc ggttggcagt gtggag                                        26

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
accatggcca tctacaagca gtcacagcac atgac                              35

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgatatcttt cttgcggaga ttctcttc                                      28

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctagcgaag ctttggtacc gtaggatcca cgaattcagt ccaggatatc ggcggtgg     58

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtttaaacg ttaaccccgg gccctcgagc tctagagcct cctccaccgc cgatatc      57

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 24

Gly Gly Gly Gly Gly
1               5

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggcggtggag gaggc                                                      15

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaattcggag ttaacgagcc caaatcttg                                       29

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggccctcat ttacccggag ac                                              22

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
actcgagatg aagacataca gtgtatc                                         27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgatatctta ggctacttca ctcaaag                                         27

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 30
tctcgagggc ggtgttctgg tgca						24

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agatatcatg tccagcgtcc agcac					25

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tctagatgag agctgttcct ctg					23

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gggcccttaa ttccgtcctt ggtg					24

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agaattcatg atgaatgatc aactcatg					28

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agcactcatc aaagtcctgg ccttggaagg gtccac				36

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
aggactttga tgagtgctat g                                          21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agggcagtct ctgaaaggca g                                          21

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cctttcagag actgccctgg cggtgttctg gtgcac                          36

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agatatcgag cagcatgagg tcgt                                       24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agatatcgag cagcatgagg tcgtg                                      25

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: This region may encompass 3 to 5 "Gly" residues

<400> SEQUENCE: 41

Gly Gly Gly Gly Gly
1               5
```